US006632449B2

(12) United States Patent
Niehoff

(10) Patent No.: US 6,632,449 B2
(45) Date of Patent: Oct. 14, 2003

(54) COMPOSITIONS AND KITS COMPRISING A DEFINED BORON COMPOUND AND METHODS OF THEIR PREPARATION

(75) Inventor: Raymond Louis Niehoff, West Chester, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/989,641

(22) Filed: Nov. 20, 2001

(65) Prior Publication Data

US 2003/0096794 A1 May 22, 2003

(51) Int. Cl.$^7$ .......................... A61K 9/08; A61K 33/22; A23L 1/30; A23L 2/00; A23L 2/02
(52) U.S. Cl. ........................ 424/439; 424/400; 424/600; 424/657; 424/659; 424/660; 426/590; 426/599; 426/648; 426/658
(58) Field of Search .................................. 424/400, 439, 424/600, 657, 659, 660; 426/590, 599, 648, 658

(56) References Cited

U.S. PATENT DOCUMENTS

| 4,849,220 A | | 7/1989 | Nielsen et al. |
|---|---|---|---|
| 5,879,698 A | | 3/1999 | Ellenbogen et al. |
| 5,962,049 A | * | 10/1999 | Miljkovic |
| 6,162,787 A | * | 12/2000 | Sorgente et al. |
| 6,413,558 B1 | * | 7/2002 | Weber et al. |
| 2001/0024658 A1 | * | 9/2001 | Chen et al. |

OTHER PUBLICATIONS

Newnham, Rex E., Ph.D., D.O., N.D.—"The Role of Boron In Human Nutrition", Journal of Applied Nutriion, vol. 46, No. 3 (1994).

* cited by examiner

Primary Examiner—Thurman K. Page
Assistant Examiner—Simon J. Oh
(74) Attorney, Agent, or Firm—S. Robert Chuey; Carl J. Roof

(57) ABSTRACT

The present disclosure is directed to compositions containing boron which are useful for a variety of purposes, including enhancing bone health, alleviating arthritis, pain, and inflammation, and producing other beneficial health effects. The disclosure is further directed to methods of preparing such compositions, methods of using (including administering) the compositions, and kits comprising the compositions. The compositions have a pH which is at least about 2 pH units less than the pKa of the boron compound.

22 Claims, No Drawings

COMPOSITIONS AND KITS COMPRISING A DEFINED BORON COMPOUND AND METHODS OF THEIR PREPARATION

FIELD OF THE INVENTION

The present invention relates to compositions containing boron which are useful for a variety of purposes, including enhancing bone health, alleviating arthritis, pain, and inflammation, and promoting other beneficial health effects. The invention is further directed to methods of preparing such compositions, methods of administering the compositions, and kits containing the compositions.

BACKGROUND OF THE INVENTION

Osteoarthritis is a widespread, degenerative disease of the joints, cartilage, and other articular components. Osteoarthritis affects all ethnic groups worldwide. In addition to humans, osteoarthritis affects nearly all mammals, for example, horses and cows, as well as domestic cats and dogs. Many treatments for osteoarthritis have been proposed, all resulting in varying degrees of success.

One osteoarthritis treatment which has been recently proposed is oral administration of chondroprotective agents such as glucosamine and/or chondroitin. See e.g., Henderson, U.S. Pat. No. 5,364,845, assigned to Nutramax Laboratories, issued Nov. 15, 1994. Indeed, various commercial products are available in the marketplace, including nutritional supplements containing such agents and powders which may be formulated into beverage compositions immediately prior to use.

Typically, administration of such agents is designed to enhance proteoglycan through an increased concentration of glycosaminoglycans. Enhanced proteoglycan provides the framework for collagen and other joint components, as well as imparting flexibility, resiliency, and resistance to compression. Thus, these agents may be administered according to various methods to enhance the articular compositions or, at a minimum, inhibit the process of degradation.

However, readily available compositions are not designed to combat all factors leading to the degradation of joints and bones. Thus, it is important to discover new compositions which more broadly meet the needs of the osteoarthritic, or pre-osteoarthritic (e.g., athletic) subject. Most recently, scientists have been studying the link between boron and the prevention or treatment of arthritis. Newnham suggests that dietary boron is related to the incidence of arthritis. See Newnham, "The Role of Boron in Human Nutrition," *Journal of Applied Nutrition*, Vol. 46, No. 3 (1994). Newnham has studied various geographies and soil conditions, and has indicated a relationship between a higher incidence of arthritis and low boron levels in soils and foods grown in such conditions. Accordingly, boron would be a useful mineral for inclusion in products which are useful for the treatment of arthritis and related conditions, either alone or in combination with other chondroprotective agents such as glucosamine and chondroitin.

In addition to these benefits, it has been shown that boron may be useful for the treatment of cancers such as prostate cancer, as well as neurological function.

Unfortunately, however, the actual formulation of boron in commercial food and beverage products, particularly beverage products, can be problematic. Indeed, the present inventor has discovered that boron can present solubility issues which make such formulation difficult, particularly with respect to low solubility in aqueous beverages. Low solubility, typically observed through precipitation of the boron in aqueous solution, leads to unpalatable or undesirable formulations in terms of appearance. Additionally, and even more problematic, this low solubility decreases the likelihood that the boron will be appropriately dosed (for example, due to settling of the boron in a beverage container, resulting in non-consumption or low consumption of the boron) and further decreases the likelihood that the boron will be solubilized and thus bioavailable to the mammal in need of treatment.

As a particular example, the present inventor has found that formulation of boron in fruit or vegetable juice matrices can be particularly difficult absent the teachings of the present invention. For example, it has been discovered that the combination of boron form and pH of the composition, when not chosen properly within the guidance of the present invention, can lead to complexation of the boron with the pectin found in such fruit or vegetable juices. Such complexes can be insoluble, leading to the foregoing issues related to unfavorable formulation, mineral delivery, and bioavailability. Moreover, improper selection of boron compound together with pH of the composition can cause unfavorable complexation with other ingredients or otherwise present solubility issues.

The present inventor has discovered that the pH and form of boron which is utilized, particularly wherein intended for use in an aqueous beverage form, should be chosen within the teachings of the present invention. In particular, the present inventor has surprisingly discovered that the pH of the composition should be at least about 2 pH units less than the pKa of the boron compound chosen for use. Proper selection of boron compounds and pH within the teachings of the present invention can therefore result in a composition which is useful for the variety of health benefits delivered by boron, including treatment for arthritis or other joint dysfunction.

The inventor has further discovered defined methods of making compositions containing a boron compound. For example, it has been surprisingly discovered that appropriate pH adjustment of a composition containing a boron compound, prior to addition of pectin (e.g., fruit or vegetable juice), carbohydrates, or other ingredients which may cause complexation or other issues, is largely important to successful formulation of the composition. These findings are indeed surprising and have not been addressed in the literature. These and other embodiments of the present invention are defined herein, which surprisingly can provide compositions containing boron which aid in dosage, compliance, and bioavailability.

SUMMARY OF THE INVENTION

In one embodiment of the invention, compositions are provided which comprise:
   a) a boron compound; and
   b) at least about 10% water, by weight of the composition; wherein the pH of the composition is at least about 2 pH units less than the pKa of the boron compound.

Methods of preparing the foregoing compositions are also provided. In particular, a preferred method of preparing a beverage composition is provided, comprising the steps of:
   a) providing an aqueous solution comprising the boron compound, wherein the pH of the aqueous solution is at least about 2 pH units less than the pKa of the boron compound and wherein the aqueous solution is substantially free of pectin and carbohydrate; and b) combining the aqueous solution with one or more additional beverage components.

Further disclosed are methods of using (including administering) the compositions, as well as kits comprising the compositions.

DETAILED DESCRIPTION OF THE INVENTION

Publications and patents are referred to throughout this disclosure. All references cited herein are hereby incorporated by reference.

All percentages and ratios are calculated by weight unless otherwise indicated. All percentages and ratios are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the methods herein.

In the description of the invention various embodiments and/or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

With respect to dosing preferences, all dosage levels are based on typical human subjects (e.g., about a 55 to 65 kg subject). Wherein the present composition is used in other mammals, it may be necessary to modify the dosage. Modification of dosages based on the needs of the subject is well within the skill of the ordinary artisan. It therefore understood that dosage ranges provided herein are by way of example only, and that daily usage can be adjusted depending on various factors. The specific dosage of the component used and duration of treatment are interdependent. The dosage and treatment regimen will also depend upon such factors as the specific compound used (e.g., the specific boron compound or chondroprotective agent), the treatment indication, the efficacy of the compound, the personal attributes of the user (such as, for example, weight, age, sex, and medical condition of the subject), and compliance with the treatment regimen.

Compositions of the Present Invention

The present invention is directed to compositions containing boron which are useful for a variety of purposes, including enhancing bone health, alleviating arthritis, pain, and inflammation, and producing other beneficial health effects. The compositions can overcome problems associated with the formulation of boron in aqueous beverages, and associated decreases in bioavailability and stability. The invention comprises several embodiments, including a variety of compositions which can overcome the problems which have been observed with respect to formulating compositions containing boron, as well as methods of producing these compounds and kits comprising the compounds.

The present invention relates to beverage compositions comprising:

(a) a boron compound; and
(b) at least about 10% water, by weight of the composition; wherein the pH of the composition is at least about 2 pH units less than the pKa of the boron compound.

There are several elements of the present invention which are common to the various embodiments herein. These include the boron compound utilized, the respective pH characteristics of the composition, and the levels of water present in the composition. These are described in further detail as follows:

The Boron Compound

The beverage compositions herein comprise a boron compound and at least about 10% water, by weight of the composition, wherein the pH of the composition is at least about 2 pH units less than the pKa of the boron compound. More preferably, the pH of the composition is at least about 2.5 pH units less than the pKa of the boron compound or at least about 3 pH units less than the pKa of the boron compound.

As has been discovered herein, the teachings herein regarding the boron compound and pH of the composition are useful for avoiding unfavorable complexation and resulting insolubility and precipitation of the compound. For example, wherein boron compounds having a relatively low pKa are utilized in slightly acidic compositions containing fruit or vegetable juice, it has been discovered that such compounds can form unfavorable complexes with the pectin which is inherently present in the juice. Such complexation can result in boron insolubility and precipitation which, in turn, imparts poor formulation capacity and poor boron bioavailability. It has been discovered that this phenomenon is completely or substantially avoided wherein the pH of the composition is at least about 2 pH units less than the pKa of the boron compound. Accordingly (for example), in acidic fruit or vegetable juices, selection of the boron compound can be critical, as well as milk beverages which typically have a higher pH relative to juice.

The boron compound utilized is therefore not limited, however, the pH of the compositions which may be utilized will depend upon the pKa of the boron compound used (and vice versa). For example, wherein a boron compound is used which has a pKa of about 9.2 (e.g., boric acid), beverage compositions having a pH of about 7.2 or less may be utilized. In contrast, wherein a boron compound is used which has a pKa of about 5.6 (e.g., boron aspartate), beverage compoisitons having a pH of about 3.6 or less may be utilized.

The pKa of any given compound is a physical property which is well understood in the art. In brief, the pKa of a given compound is a measure of the pH at which the compound is half dissociated, which is readily measured by one of ordinary skill in the art. The boron compound having the appropriate pKa values, depending upon the desired pH of the beverage composition, will therefore be well understood to one of ordinary skill in the art using the guidance herein and known determination of pKa values. For example, use of simple titration procedures may be utilized to determine whether a particular boron compound is suitable for use in the present invention. See e.g., Atkins, *Physical Chemistry*, 5$^{th}$ Ed., ISBN 0-7167-2402-2, pp. 291–298 (1994).

Preferred boron compounds have a pKa of about 4 or greater. In an additionally preferred mode of the invention, the pKa of the boron compound is about 6 or greater, 7.5 or greater, or even about 9 or greater.

Non-limiting examples of boron compounds suitable for use herein include boric acid (having a pKa of about 9.2), sodium borate (e.g., BORAX®) (having a pKa of about 9.2), boron citrate (having a pKa of about 7.5), boron glycinate (having a pKa of about 4.9), and boron aspartate (having a pKa of about 5.6). The most preferred boron compounds for use herein are boric acid and boron citrate.

In accordance with the present invention, a single serving of the composition (about 236 mL) preferably comprises from about 0.001 milligrams to about 20 milligrams, more preferably from about 0.1 milligrams to about 15 milligrams, even more preferably from about 0.5 milligrams to about 10 milligrams, and most preferably from about 2 milligrams to about 5 milligrams of boron, wherein the composition is intended for typical human use.

Typically, the composition is dosed from about once to about five times daily. However, a typical dosage can be dosed such that dosing need only occur about once or twice daily, preferably once daily. Thus, compliance and consumer benefit can be enhanced. As used herein, a single serving, used for a single dose of the composition, is typically about 236 milliliters of the composition.

Alternatively or additionally, the compositions preferably comprise from about 0.00001% to about 1%, more preferably from about 0.00005% to about 0.5%, even more preferably from about 0.0001% to about 0.01%, still more preferably from about 0.0001% to about 0.008%, and most preferably from about 0.0001% to about 0.005% of the boron compound, all by weight of the composition.

pH

As has been stated, the compositions used herein will have a pH which is at least about 2 pH units less than the pKa of the boron compound used. As has been discovered herein, compositions having this defined pH will be optimal for use herein in order that complexation, insolubility, and/or precipitation of a boron compound is avoided or minimized, and ease of formulation and favorable bioavailability is achieved.

Preferably, the compositions have a pH of about 7.2 or less, even more preferably about 6 or less, and most preferably about 5 or less. At acidic pH, it has been discovered that the present invention is optimally utilized at a pH of from about 2.5 to about 4.

If necessary to adjust the pH of the composition utilized, the compositions may optionally comprise one or more acidulants. Acidity can be adjusted to and maintained within the requisite range by known and conventional methods, e.g., the use of one or more acidulants. Typically, acidity within the above recited ranges is a balance between maximum acidity for microbial inhibition and optimum acidity for the desired beverage flavor.

Organic as well as inorganic edible acids may be used to adjust the pH of the composition. The acids can be present in their undissociated form or, alternatively, as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric acid and/or malic acids.

The acidulant can also serve as an antioxidant to stabilize beverage components. Examples of commonly used antioxidant include but are not limited to ascorbic acid, EDTA (ethylenediaminetetraacetic acid), and salts thereof.

However, in some cases acidic components need not be used. For example, the present compositions may inherently have the required pH without use of any components which tend to modify such pH.

Water

Preferred beverage compositions herein are beverage concentrates and ready-to-drink beverage compositions. The compositions used herein comprise at least about 10% water, by weight of the composition. More preferably, the compositions comprise at least about 40% water, still more preferably at least about 50% water, even more preferably at least about 75% water, and most preferably at least about 80% water, all by weight of the composition. Still further, ready-to-drink beverage compositions will typically comprise at least about 82% water, more typically at least about 85% water, all by weight of the composition. The water present in a given composition includes all added water and any water inherently present in other components, for example, fruit or vegetable juice.

Various Embodiments of the Present Invention

As stated, there are various embodiments of the present invention which may be utilized in accordance with the present discovery. Preferred pKa values, pH levels, and water levels are as stated herein above. Such compositions may optionally contain any further components including, but not limited to, the preferred optional components described herein below.

Additionally, in certain embodiments, the compositions may be (but need not be) substantially free of boron-carbohydrate complexes. Such boron-carbohydrate complexes are described in, for example, Miljkovic, U.S. Pat. No. 5,962,049, issued Oct. 5, 1999. In reference to such boron-carbohydrate complexes, the term "substantially free" means that the compositions may comprise such boron-carbohydrate complexes, but only such complexes having a boron-ligand association constant of less than about 250, more preferably less than about 200, and/or that the compositions comprise less than about 1%, more preferably less than about 0.5%, and most preferably less than about 0.1% of boron-carbohydrate complexes having a boron-ligand association constant of about 250 (or, 200) or greater, all by weight of the composition. See Miljkovic, U.S. Pat. No. 5,962,049, issued Oct. 5, 1999, for description of boron-ligand association constant.

As has been discovered herein, avoidance of boron complex formation does not require avoidance of compounds which may ordinarily complex with the boron compound, such as a carbohydrate. Rather, as has been discovered herein, the present compositions may provide boron compounds which remain uncomplexed, even in the presence of one or more carbohydrates such as, for example, sucrose, fructose, mannose, xylose, or sorbose, or other susceptible ingredients such as pectin.

This may be achieved by a variety of mechanisms, for example, via the method of preparation described further herein. It has been discovered that providing boron compounds which are not complexed with another ingredient provides a variety of unique benefits including, for example, avoidance of further complexation with compounds such as pectin (found in fruit or vegetable juice) and avoidance of insolubility and precipitation of the boron compound. These unique benefits lead to enhanced formulation of boron-containing compositions and enhanced boron bioavailability.

Therefore, in a particularly preferred embodiment herein, the composition comprises pectin. It has been discovered that, absent the teachings of the present invention, pectin can unfavorably complex with the boron compound. Such complexation can lead to insolubility and precipitation of the complex which, in turn, can result in inability to properly formulation beverage compositions containing such boron-containing ingredients. However, through use of the appropriate boron compounds and pH levels as described herein, these problems have been surprisingly overcome.

As a result, it has been discovered that boron may be combined with pectin with more ease of formulation and enhanced bioavailability of the boron using the guidance of the present invention. This is particularly important in compositions containing fruit or vegetable juices, which typically contain pectin. Accordingly, in a particularly preferred example of this embodiment, the compositions comprise fruit and/or vegetable juice, most preferably fruit juice.

Wherein fruit or vegetable juice is included, the compositions of the present invention can comprise from about 0.1% to about 99%, preferably from about 1% to about 50%, more preferably from about 2% to about 15%, and most preferably from about 3% to about 6%, fruit or vegetable juice. (As measured herein, the weight percentage of juice is based on a single strength 2° to 16° Brix juice). The juice can be incorporated into the composition as a puree, comminute, or as a single strength or concentrated juice. Especially preferred is incorporation of the juice as a concentrate with a solids content (primarily as sugar solids) of from about 20° to about 80° Brix.

Juices will be well understood in the art and may be derived from, for example, apple, cranberry, pear, peach, plum, apricot, nectarine, grape, cherry, currant, raspberry, gooseberry, elderberry, blackberry, blueberry, strawberry, lemon, lime, mandarin, orange, grapefruit, cupuacu, potato, tomato, lettuce, celery, spinach, cabbage, watercress, dandelion, rhubarb, carrot, beet, cucumber, pineapple, coconut, pomegranate, kiwi, mango, papaya, banana, watermelon, passion fruit, tangerine, and cantaloupe. Preferred juices are derived from apple, pear, lemon, lime, mandarin, grapefruit, cranberry, orange, strawberry, tangerine, grape, kiwi, pineapple, passion fruit, mango, guava, raspberry and cherry. Citrus juices, preferably grapefruit, orange, lemon, lime, and mandarin juices, as well as juices derived from mango, apple, passion fruit, and guava, as well as mixtures of these juices are most preferred.

In yet another preferred embodiment of the present invention, the compositions herein may comprise a further chondroprotective agent. As has been described herein, boron is useful for a variety of health benefits including, for example, enhancing bone health, alleviating arthritis, pain, and inflammation, and producing other beneficial health effects. As has been discovered herein, the boron compounds of the composition may be optimally combined with one or more further chondroprotective agents to provide synergistic health effects, particularly in the field of bone health, arthritis, pain relief, and ant-inflammation.

Chondroprotective agents are well-known in the art. Preferred chondroprotective agents for use herein include those selected from the group consisting of gelatin, cartilage, aminosugars, glycosaminoglycans, methylsulfonylmethane, precursors of methylsulfonylmethane, S-adenosylmethionine, salts thereof, and mixtures thereof.

Without intending to be limited by theory, the chondroprotective agent is useful for further enhancing joint function as the agent aids in the stimulation of proteoglycan and collagen in vivo. Proteoglycan provides the connective tissue, for example, collagen, which is necessary for joint health. Indeed, proteoglycan is comprised of glycosaminoglycans (often termed "GAGs") which are long chains of modified sugars. Aminosugars and methylsulfonylmethane are useful for building glycosaminoglycans and proteoglycan. Additionally, the cardiac benefits of various of these components is also a beneficial feature of this component. See e.g., Morrison et al., Coronary Heart Disease and the Mucopolysaccharides (Glycosaminoglycans), pp. 109–127 (1973).

Preferably, the agent is selected from gelatin, cartilage, aminosugars, glycosaminoglycans, S-adenosylmethionine, salts thereof, and mixtures thereof. More preferably, the agent is selected from aminosugars, glycosaminoglycans, S-adenosylmethionine, salts thereof, and mixtures thereof. Even more preferably, the agent is selected from aminosugars, glycosaminoglycans, salts thereof, and mixtures thereof. Aminosugars and salts thereof are particularly preferred. Most preferably, the agent is a salt of an aminosugar, particularly wherein the aminosugar is glucosamine.

In addition or as an alternate to the preferred dosing levels described below for each individual exemplified chondroprotective agent, the compositions herein typically comprise from about 0% to about 10%, more preferably from about 0.0001% to about 5%, still more preferably from about 0.001% to about 3%, even more preferably from about 0.1% to about 2%, and most preferably from about 0.2% to about 1% of the chondroprotective agent, all by weight of the composition.

The various chondroprotective agents, and preferred embodiments thereof, are described in expanded detail as follows:

As is commonly known, gelatin is a protein obtained from the partial hydrolysis of collagen, which is the major structural and connective protein tissue in mammals. Gelatin typically contains from about 84% to about 90% protein, from about 1% to about 2% mineral salts, and from about 8% to about 15% water (these are non-limiting approximations). Gelatin typically contains specific amounts of 18 different amino acids, which are joined together to form polypeptide chains of approximately 1,000 amino acid residues per chain.

Typically, the collagen obtained for gelatin production is from animal bones and skins, e.g., from cows and pigs. Gelatin production will typically involve the subjection of collagenous material to alkaline pre-treatment, followed by hot-water extraction (providing gelatin having an isoelectric point of about 5). Acidic pre-treatment may also be utilized (providing gelatin having an isoelectric point of from about 7 to about 9).

In accordance with the present invention, wherein gelatin is included within a present composition, a single serving of the composition herein preferably comprises from about 1 milligram to about 2000 milligrams, more preferably from about 100 milligrams to about 700 milligrams, even more preferably from about 150 milligrams to about 600 milligrams, and most preferably from about 200 milligrams to about 400 milligrams of the gelatin. Typically, the composition comprising gelatin is dosed from about once to about five times daily. However, in the food and beverage composition embodiments of the present invention, which are preferred, a typical dosage can be dosed such that dosing need only occur about once daily. Thus, in these food and beverage compositions, compliance and consumer benefit is enhanced. As used herein, a single serving of the composition is about 236 milliliters of the composition.

Cartilage may be chosen as the agent in the present compositions. As is commonly known in the art, cartilage is a tough, elastic tissue present in the joints (as well as other locations) of the bodies of various mammals. Cartilage is comprised of at least one of calcium, proteins, carbohydate mucopolysaccharides (e.g., chondroitin), and collagen.

Particularly preferred for use herein is bovine cartilage and shark cartilage. Bovine cartilage is primarily derived from the trachea of cows (also known as bovine tracheal cartilage, or BTC). It is similar in structure to shark cartilage. Shark cartilage is a widely utilized cartilage source, as the skeletons of sharks are primarily composed of cartilage rather than bone.

In accordance with the present invention, wherein cartilage is included within a present composition, a single serving of the composition herein preferably comprises from about 1 milligram to about 2000 milligrams, more preferably from about 100 milligrams to about 700 milligrams, even more preferably from about 150 milligrams to about 600 milligrams, and most preferably from about 200 milligrams to about 400 milligrams of the cartilage. Typically, the composition comprising cartilage is dosed from about once to about five times daily. However, in the food and beverage composition embodiments of the present invention, which are preferred, a typical dosage can be dosed such that dosing need only occur about once daily. Thus, in these food and beverage compositions, compliance and consumer benefit is enhanced. As used herein, a single serving of the composition is about 236 milliliters of the composition.

One or more aminosugars may be chosen as the agent herein. The aminosugars are monosaccharide components (i.e., hexoses) which are modified with an amine functionality. The amine functionality may be a free amine moiety or a protected amine moiety (e.g., N-acetyl amine). Preferably, the aminosugar is a precursor to glycosaminoglycan, which is important for construction of joint constituents (e.g., collagen). Additionally, certain aminosugars may serve to inhibit the activity of enzymes which are implicated in breakdown the cartilage in osteoarthritics (e.g., mannosamine, which has been discovered to inhibit aggrecanase). The aminosugars are well-known in the art; many aminosugars are naturally occurring.

Particularly preferred aminosugars include glucosamine, salts of glucosamine, galactosamine, salts of galactosamine, mannosamine, salts of mannosamine, as well as the N-acetyl derivatives of the foregoing, including N-acetyl glucosamine and N-acetyl galactosamine. More preferably, the aminosugars include glucosamine and salts of glucosamine, most preferably salts of glucosamine. Particularly preferred salts of glucosamine include glucosamine sulfate and glucosamine hydrochloride. The salts of glucosamine are particularly preferred to aid bioavailability of the aminosugar in addition to the bioavailability benefit achieved by the second component (as described herein below).

As an example, glucosamine provides the building block needed in vivo to manufacture glycosaminoglycan, which is found in cartilage. Thus, glucosamine, and other aminosugars, function not only to relieve symptoms of joint pain but also stop, inhibit, and/or reverse the degenerative process.

Wherein an amino sugar is used herein, a single serving of the composition preferably comprises from about 1 milligram to about 5000 milligrams, more preferably from about 100 milligrams to about 3600 milligrams, even more preferably from about 150 milligrams to about 2200 milligrams, and most preferably from about 1400 milligrams to about 1900 milligrams of the aminosugar, based on the molecular weight of glucosamine hydrochloride. For example, a particularly preferred once daily dosage of glucosamine hydrochloride is about 1800 milligrams, which translates to about 1480 milligrams of glucosamine. Typically, the composition comprising the aminosugar is dosed from about once to about five times daily, preferably from about once to about three times daily. However, in the food and beverage composition embodiments of the present invention, which are preferred, a typical dosage can be dosed such that dosing need only occur about once daily. As used herein, a single serving of the composition is about 236 milliliters of the composition.

One or more glycosaminoglycans may be utilized as the agent herein. The glycosaminoglycans are commonly known as GAGs, and are precursors to joint structure, for example, proteoglycan. The glycosaminoglycans may also be important for the healing of bone.

Suitable glycosaminoglycans will be well-known to the ordinarily skilled artisan. Preferred glycosaminoglycans include chondroitin, hyaluronic acid, keratan, heparin, and dermatin, as well as salts of the foregoing. For example, chondroitin sulfate is a particularly preferred chondroitin salt. As with the aminosugars, salts of the glycosaminoglycans are particularly preferred for use herein.

As an example, chondroitin provides the structure and allows various molecules to transport through cartilage (which is important, since there is no blood supply to cartilage). Chondroitin is a major constituent of cartilage and contains repeating chains of saccharides.

Wherein a glycosaminoglycan is used herein, a single serving of the composition preferably comprises from about 1 milligram to about 10 grams, more preferably from about 100 milligrams to about 5 grams, even more preferably from about 150 milligrams to about 1000 milligrams, and most preferably from about 250 milligrams to about 800 milligrams of the glycosaminoglycan, based on the molecular weight of chondroitin. Typically, the composition comprising the glycosaminoglycan is dosed from about once to about five times daily. However, in the food and beverage composition embodiments of the present invention, which are preferred, a typical dosage can be dosed such that dosing need only occur about once daily. As used herein, a single serving of the composition is about 236 milliliters of the composition.

The agent herein may also be methylsufonylmethane, or a precursor thereof. As used herein, the term "precursor thereof" means a compound which, in mammalian systems, is converted to methylsulfonylmethane in vivo. Methylsulfonylmethane, and precursors thereof, are common ingredients found in vivo and in nature, e.g., in unprocessed foods. Without intending to be limited by theory, it is believed that the sulfur moiety present in methylsulfonylmethane, and its precursors, provides the disulfide bridging (also commonly known as "tie-bars" or "cross-links") necessary to hold the connective tissue in joints together.

While unprocessed foods contain methylsulfonylmethane, and the precursors thereof, conventional food processing and preparation causes the loss of these compounds from the foods. Therefore, commonly ingested foods may become deficient in these compounds. In these respects, methylsulfonylmethane is similar to vitamins and minerals which are typically partially or totally lost during normal food processing and preparation. It is therefore an important embodiment of this invention to include, as the agent, methylsulfonylmethane or a precursor thereof in the present compositions.

Non-limiting examples of precursors of methylsulfonylmethane include methionine and methyl sulfide. See e.g., Herschler et al., U.S. Pat. No. 4,863,748, issued Sep. 5, 1989. Precursors of methylsulfonylmethane is associated with a variety of health benefits, including joint benefits (such as relief from osteoarthritis and rheumatoid arthritis), as well as anti-inflammation.

In accordance with the present invention, wherein methanesulfonylmethane is included within a present composition, a single serving of the composition herein preferably comprises from about 0.01 milligrams to about 2000 milligrams, more preferably from about 0.01 milligrams to about 500 milligrams, even more preferably from about 1 milligram to about 200 milligrams, and most preferably from about 1 milligram to about 100 milligrams. The precursors of methanesulfonylmethane may be similarly dosed, based on the molecular weights of the precursors relative to methanesulfonylmethane. Typically, the composition comprising methanesulfonylmethane is dosed from about once to about five times daily. However, in the food and beverage composition embodiments of the present invention, which are preferred, a typical dosage can be dosed such that dosing need only occur about once daily. As used herein, a single serving of the composition is about 236 milliliters of the composition.

S-adenosylmethionine, which is commonly known as SAM-e, is a compound which is found in most, if not all, living cells. Without intending to be limited by theory, SAM-e is produced through reaction of the essential amino acid methionine and the energy molecule known as adenosine triphosphate (commonly known as ATP). SAM-e manufactures the components of cartilage and repairs, restores, and maintains joint function. SAM-e is made in vivo from the amino acid methionine, and is found in ordinary dietary sources such as meats, soybeans, eggs, seeds, and lentils.

In accordance with the present invention, wherein SAM-e is included within a present composition, a single serving of the composition herein preferably comprises from about 1 milligram to about 2000 milligrams, more preferably from about 100 milligrams to about 700 milligrams, even more preferably from about 150 milligrams to about 600 milligrams, and most preferably from about 200 milligrams to about 400 milligrams. Typically, the composition comprising SAM-e is dosed from about once to about five times daily. However, in the food and beverage composition embodiments of the present invention, which are preferred, a typical dosage can be dosed such that dosing need only occur about once daily. As used herein, a single serving of the composition is about 236 milliliters of the composition.

Other Optional Components of the Present Compositions

As stated, the compositions of the present invention may be utilized as beverage compositions and therefore may contain a variety of optional components. Pectin (e.g., as fruit or vegetable juice) and chondroprotective agents are particularly preferred and have already been described. Moreover, the compositions of the present invention may comprise other optional components to enhance, for example, their performance in providing one or more of the foregoing health benefits (for example, arthritis relief), providing a desirable nutritional profile, and/or providing enhanced organoleptic properties. Such optional components may be dispersed, solubilized, or otherwise mixed into the present compositions. Non-limiting examples of other optional components suitable for use herein are given below.

Flavanols

Flavanols are natural substances present in a variety of plants (e.g., fruits, vegetables, and flowers). The flavanols which may be utilized in the present invention can be extracted from, for example, fruit, vegetables, green tea or other natural sources by any suitable method well known to those skilled in the art. For example, extraction with ethyl acetate or chlorinated organic solvents is a common method to isolate flavanols from green tea. Flavanols may be extracted from either a single plant or mixtures of plants. Many fruits, vegetables, and flowers contain flavanols but to a lesser degree relative to green tea. Plants containing flavanols are known to those skilled in the art. Examples of the most common flavanols which are extracted from tea plants and other members of the *Catechu gambir* (Uncaria family) include, for example, catechin, epicatechin, gallocatechin, epigallocatechin, epicatechin gallate, and epigallocatechin gallate.

The flavanols utilized in all compositions of the present invention can be in the form of a tea extract. The tea extract can be obtained from the extraction of unfermented teas, fermented teas, partially fermented teas, and mixtures thereof. Preferably, the tea extracts are obtained from the extraction of unfermented and partially fermented teas. The most preferred tea extracts are obtained from green tea. Both hot and cold extracts can be used in the present invention. Suitable methods for obtaining tea extracts are well known. See e.g., Ekanayake, U.S. Pat. No. 5,879,733, issued Mar. 9, 1999; Tsai, U.S. Pat. No. 4,935,256, issued June, 1990; Lunder, U.S. Pat. No. 4,680,193, issued July, 1987; and Creswick, U.S. Pat. No. 4,668,525, issued May 26, 1987.

The preferred source of flavanols in the compositions of the present invention is green tea. Wherein green tea, and in particular the flavanols present in green tea, are incorporated into the beverage, the present inventor has discovered that the flavanols are at least partially responsible for delaying the bioavailability of bracers, which contributes to the reduction and/or elimination of nervousness and tension typically associated with such bracers.

Alternatively, these same flavanols may be prepared by synthetic or other appropriate chemical methods and incorporated into the present compositions. Flavanols, including catechin, epicatechin, and their derivatives are commercially available.

The amount of flavanols in the compositions of the present invention can vary. However, wherein one or more flavanols are utilized, preferably from about 0.001% to about 5%, more preferably from about 0.001% to about 2%, even more preferably from about 0.01% to about 1%, and most preferably from about 0.01% to about 0.05% of one or more flavanols is utilized, by weight of the composition.

Sweeteners

The compositions of the present invention can, and typically will, contain an effective amount of one or more sweeteners, including carbohydrate sweeteners and natural and/or artificial no/low calorie sweeteners. The amount of the sweetener used in the beverages of the present invention typically depends upon the particular sweetener used and the sweetness intensity desired. For no/low calorie sweeteners, this amount varies depending upon the sweetness intensity of the particular sweetener.

The compositions of the present invention can be sweetened with any of the carbohydrate sweeteners, preferably monosaccharides and/or disaccharides. These sugars can be incorporated into the beverages in solid or liquid form but are typically, and preferably, incorporated as a syrup, most preferably as a concentrated syrup such as high fructose corn syrup. For purposes of preparing beverages of the present invention, these sugar sweeteners can be provided to some extent by other components of the beverage such as, for example, the fruit juice component and/or flavors.

Preferred sugar sweeteners for use in beverage products of the present invention are sucrose, fructose, glucose, and mixtures thereof, particularly sucrose and fructose. Fructose can be obtained or provided as liquid fructose, high fructose corn syrup, dry fructose or fructose syrup, but is preferably provided as high fructose corn syrup. High fructose corn syrup (HFCS) is commercially available as HFCS-42, HFCS-55 and HFCS-90, which comprise 42%, 55% and 90%, respectively, by weight of the sugar solids therein, as fructose. Other naturally occurring sweeteners or their purified extracts, such as glycyrrhizin, stevioside, the protein sweetener thaumatin, the juice of Luo Han Guo (containing the sweet mogrosides) disclosed in, for example, Fischer et al., U.S. Pat. No. 5,433,965, issued Jul. 18, 1995, and the like can also be used in the beverages of the present invention.

Effective levels of non-caloric sweeteners may optionally be used in the compositions of the present invention to further sweeten such compositions. Non-limiting examples of non-caloric sweeteners include aspartame, saccharine, cyclamates, acesulfame K, L-aspartyl-L-phenylalanine lower alkyl ester sweeteners, L-aspartyl-D-alanine amides such as, for example, those disclosed in Brennan et al., U.S. Pat. No. 4,411,925, issued 1983, L-aspartyl-D-serine amides such as, for example, those disclosed in Brennan et al., U.S. Pat. No. 4,399,163, issued 1983, L-aspartyl-hydroxymethyl alkane amide sweeteners such as, for example, those disclosed in Brand, U.S. Pat. No. 4,338,346, issued 1982, L-aspartyl-1-hydroxyethylalkane amide sweeteners such as, for example, those disclosed in Rizzi, U.S. Pat. No. 4,423,029, issued 1983, glycyrrhizins, and synthetic alkoxy aromatics. Aspartame and acesulfame-K are the most preferred non-caloric sweeteners utilized herein, and may be utilized alone or in combination.

Wherein one or more sweeteners are utilized herein, the total sweetener is preferably utilized at various levels, particularly depending upon the sweetness desired and/or whether the beverage composition is a ready-to-drink beverage composition or a beverage concentrate. Typical levels may range from about 0.0001% to about 50%, 0.001% to about 20%, 0.001% to about 15%, 0.005% to about 11%, 1% to about 10%, or from about 5% to about 9%, by weight of the composition.

Nutrients

The compositions herein may optionally be fortified with one or more vitamins or minerals, which are referred to herein as nutrients. The U.S. Recommended Daily Intake (USRDI) for vitamins and minerals is defined and set forth in the Recommended Daily Dietary Allowance-Food and Nutrition Board, National Academy of Sciences-National Research Council. Unless otherwise specified herein, wherein a given vitamin is present in the composition, the composition comprises at least about 1%, preferably at least about 5%, more preferably from about 10% to about 200%, even more preferably from about 10% to about 150%, and most preferably from about 10% to about 100% of the USRDI of such vitamin. Unless otherwise specified herein, wherein a given mineral other than boron is present in the composition, the composition typically comprises at least about 1%, preferably at least about 5%, more preferably from about 5% to about 100%, even more preferably from about 10% to about 40%, and most preferably from about 10% to about 30% of the USRDI of such mineral.

Non-limiting examples of vitamins include vitamin A, one or more B-complex vitamins (which include one or more of thiamine (also commonly referred to as "vitamin $B_1$"), riboflavin (also commonly referred to as "vitamin $B_2$"), niacin (also commonly referred to as "vitamin $B_3$"), pantothenic acid (also commonly referred to as "vitamin $B_5$"), pyridoxine (also commonly referred to as "vitamin $B_6$"), biotin, folic acid (also commonly referred to as folate), and the cobalamins (also commonly referred to as "vitamin $B_{12}$")), vitamin C, vitamin D, and vitamin E. Preferably, at least one vitamin is selected from vitamin A, niacin, thiamine, folic acid, pyroxidine, pantothenic acid, vitamin C, vitamin E, and vitamin D. Preferably, at least one vitamin is selected from vitamin A, thiamine, pyroxidine, pantothenic acid, vitamin C, and vitamin E.

As used herein, "vitamin A" is inclusive of one or more nutritionally active unsaturated hydrocarbons, including the retinoids (a class of compounds including retinol and its chemical derivatives having four isoprenoid units) and the carotenoids. Common retinoids include retinol, retinal, retinoic acid, retinyl palmitate, and retinyl acetate.

In a preferred embodiment herein, the vitamin A is a carotenoid. Common carotenoids include beta-carotene, alpha-carotene, beta-apo-8'-carotenal, cryptoxanthin, canthaxanthin, astacene, and lycopene. Among these, beta-carotene is the most preferred for use herein.

The vitamin A may be in any form, for example, an oil, beadlets, or encapsulated. See e.g., Cox et al., U.S. Pat. No. 6,007,856, assigned to The Procter & Gamble Co., issued Dec. 28, 1999. Vitamin A is often available as an oil dispersion, i.e., small particles suspended in oil.

Wherein vitamin A is present in the compositions herein, the composition typically comprises, per single serving of the composition (typically, about 236 milliliters of total composition), at least about 1%, preferably at least about 5%, more preferably from about 10% to about 200%, even more preferably from about 15% to about 150%, and most preferably from about 20% to about 120% of the USRDI of such vitamin. Wherein vitamin A is present in the compositions herein, it is especially preferred to include about 25% of the USRDI of vitamin A, per single serving of the composition. Alternatively, the compositions preferably comprise from 0% to about 1%, more preferably from about 0.0002% to about 0.5%, also preferably from about 0.0003% to about 0.25%, even more preferably from about 0.0005% to about 0.1%, and most preferably from about 0.001% to about 0.08% of vitamin A, by weight of the composition. The ordinarily skilled artisan will understand that the quantity of vitamin A to be added is dependent on processing conditions and the amount of vitamin A delivery desired after storage.

As stated the vitamin used herein may be a B-complex vitamin. As used herein, the B-complex vitamins include one or more of thiamine (also commonly referred to as "vitamin $B_1$"), riboflavin (also commonly referred to as "vitamin $B_2$"), niacin (also commonly referred to as "vitamin $B_3$"), pantothenic acid (also commonly referred to as "vitamin $B_5$"), pyridoxine (also commonly referred to as "vitamin $B_6$"), biotin, folic acid (also commonly referred to as folate), and the cobalamins (also commonly referred to as "vitamin $B_{12}$"). Among these, inclusion of vitamin $B_1$ and/or $B_6$ are particularly preferred.

Wherein a B-complex vitamin is present in the compositions herein, the composition typically comprises at least about 1%, preferably at least about 5%, more preferably from about 10% to about 200%, even more preferably from about 15% to about 150%, and most preferably from about 20% to about 120% of the USRDI of each B-complex vitamin present in the composition, per single serving of the composition (typically, about 236 milliliters of total composition). Wherein a B-complex vitamin is present in the compositions herein, it is especially preferred to include from about 10% to about 50% of the USRDI of each B-complex vitamin present in the composition, per single serving of the composition. Alternatively, wherein a B-complex vitamin is included within the present compositions, the compositions typically comprise from 0% to about 2%, more preferably from about 0.0002% to about 1%, also preferably from about 0.0005% to about 0.2%, even more preferably from about 0.001% to about 0.1%, and most preferably from about 0.001% to about 0.1% of each B-complex vitamin present in the composition, by weight of the composition. The ordinarily skilled artisan will understand that the quantity of B-complex vitamin to be added is dependent on processing conditions and the amount of B-complex vitamin delivery desired after storage.

As used herein, "vitamin C" is inclusive of one or more of L-ascorbic acid, as well as their bioequivalent forms including salts and esters thereof. For example, the sodium salt of L-ascorbic acid is considered vitamin C herein. Additionally, there are many widely known esters of vitamin C, including ascorbyl acetate. Fatty acid esters of vitamin C are lipid soluble and can provide an antioxidative effect.

The vitamin C utilized may be in any form, for example, free or in encapsulated form.

Wherein vitamin C is present in the compositions herein, the composition typically comprises at least about 1%, preferably at least about 5%, more preferably from about 10% to about 200%, even more preferably from about 15% to about 150%, and most preferably from about 20% to about 120% of the USRDI of such vitamin, per single serving of the composition (typically, about 236 milliliters of total composition). Wherein vitamin C is present in the compositions herein, it is especially preferred to include about 100% of the USRDI of vitamin C, per single serving of the composition. Alternatively, wherein vitamin C is included within the present compositions, the compositions typically comprise from 0% to about 2%, more preferably from about 0.0002% to about 1%, also preferably from about 0.0003% to about 0.5%, even more preferably from about 0.0005% to about 0.2%, and most preferably from about 0.001% to about 0.1% of vitamin C, by weight of the composition. The ordinarily skilled artisan will understand that the quantity of vitamin C to be added is dependent on processing conditions and the amount of vitamin C delivery desired after storage.

As used herein, "vitamin E" is inclusive of one or more tocols or tocotrienols which exhibit vitamin activity similar to that of alpha-tocopherol (which, as used herein, is considered a tocol) as well as their bioequivalent forms including salts and esters thereof. Vitamin E is typically found in oils including, for example, sunflower, peanut, soybean, cottonseed, corn, olive, and palm oils.

Non-limiting examples of vitamin E include alpha-tocopherol, beta-tocopherol, gamma-tocopherol, and delta-tocopherol, as well as esters thereof (e.g., alpha-tocopherol acetate). Alpha-tocopherol and particularly alpha-tocopherol acetate are highly preferred for use as vitamin E herein.

The vitamin E utilized may be in any form, for example, free or in encapsulated form. Wherein vitamin E is present in the compositions herein, the composition typically comprises at least about 1%, preferably at least about 5%, more preferably from about 10% to about 200%, even more preferably from about 15% to about 150%, and most preferably from about 20% to about 120% of the USRDI of such vitamin, per single serving of the composition (typically, about 236 milliliters of total composition). Wherein vitamin E is present in the compositions herein, it is especially preferred to include about 25% of the USRDI of vitamin E, per single serving of the composition. Alternatively, wherein vitamin E is included within the present compositions, the compositions typically comprise from 0% to about 2%, more preferably from about 0.0002% to about 1%, also preferably from about 0.0003% to about 0.2%, even more preferably from about 0.0005% to about 0.1%, and most preferably from about 0.001% to about 0.1% of vitamin E, by weight of the composition. The ordinarily skilled artisan will understand that the quantity of vitamin E to be added is dependent on processing conditions and the amount of vitamin E delivery desired after storage.

Minerals other than boron are well-known in the art. Non-limiting examples of such minerals include zinc, iron, magnesium, calcium, selenium, iodine, and fluoride. Preferably, wherein a mineral is utilized, at least one mineral is selected from zinc, magnesium, iron, iodine, and calcium. Most preferably, at least one mineral is selected from zinc, iron, magnesium, and calcium. Iron and calcium are particularly preferred for use herein. Minerals may be, for example, salts, chelated, encapsulated, or in colloidal form.

As used herein, "zinc" is inclusive of any compound containing zinc, including a salt, complex, or other form of zinc, including elemental zinc. Acceptable forms of zinc are well-known in the art. The zinc which can be used in the present invention can be in any of the commonly used forms such as, e.g., zinc lactate, zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred. Additionally, it has been found that amino acid chelated zinc is most highly preferred, as this zinc form provides optimized bioavailability of the zinc, other minerals present within the composition, as well as optimizing the bioavailability of the arabinogalactan utilized in the composition.

Amino acid chelates of zinc are well-known in the art, and are described in, for example, Pedersen et al., U.S. Pat. No. 5,516,925, assigned to Albion International, Inc., issued May 14, 1996; Ashmead, U.S. Pat. No. 5,292,729, assigned to Albion International, Inc., issued Mar. 8, 1994; and Ashmead, U.S. Pat. No. 4,830,716, assigned to Albion International, Inc., issued May 16, 1989. These chelates contain one or more natural amino acids selected from alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine or dipeptides, tripeptides or quadrapeptides formed by any combination of these amino acids.

Additionally, encapsulated zinc is also preferred for use herein. For example, the zinc may be encapsulated with bilayer-forming emulsifiers. See Mehansho et al., U.S. Pat. No. 5,888,563, issued Mar. 30, 1999.

Zinc fortified compositions of the present invention typically contain at least about 1 milligram of zinc, more preferably at least about 5 milligrams of zinc, and most preferably at least about 10 milligrams of zinc, all per single serving of the composition (typically, about 236 milliliters of total composition). Typically, from about 10 milligrams to about 25 milligrams of zinc per single serving is recommended. Alternatively, the present compositions preferably comprise from 0% to about 0.1%, more preferably from about 0.001% to about 0.08%, even more preferably from about 0.002% to about 0.05%, and most preferably from about 0.002% to about 0.03% of the zinc-containing component, by weight of the composition.

As used herein, "iron" is inclusive of any compound containing iron, including a salt, complex, or other form of iron, including elemental iron. Acceptable forms of iron are well-known in the art.

Non-limiting examples of ferrous iron sources which can be used in the present invention include ferrous sulfate, ferrous fumarate, ferrous succinate, ferrous gluconate, ferrous lactate, ferrous tartrate, ferrous citrate, ferrous amino acid chelates, and ferrous pyrophsophate, as well as mixtures of these ferrous salts. While ferrous iron is typically more bioavailable, certain ferric salts can also provide highly bioavailable sources of iron. Non-limiting examples of ferric iron sources that can be used in the present invention are ferric saccharate, ferric ammonium citrate, ferric citrate, ferric sulfate, ferric chloride, and ferric pyrophosphate, as well as mixtures of these ferric salts. A particularly preferred ferric iron source is ferric pyrophosphate, for example, microencapsulated SUNACTIVE® Iron, commercially available from Taiyo International, Inc., Edina, Minn., U.S.A and Yokkaichi, Mie, Japan. SUNACTIVE® Iron is particularly preferred for use herein due to its water-dispersibility, particle size, compatibility, and bioavailability.

Ferrous amino acid chelates particularly suitable as highly bioavailable amino acid chelated irons for use in the present invention are those having a ligand to metal ratio of at least 2:1. For example, suitable ferrous amino acid chelates having a ligand to metal mole ratio of two are those of formula:

$$Fe(L)_2$$

where L is an alpha amino acid, dipeptide, tripeptide or quadrapeptide reacting ligand. Thus, L can be any reacting ligand that is a naturally occurring alpha amino acid selected from alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine and valine or dipeptides, tripeptides or quadrapeptides formed by any combination of these amino acids. See e.g., U.S. Pat. No. 5,516,925; U.S. Pat. No. 5,292,729; and U.S. Pat. No. 4,830,716. Particularly preferred ferrous amino acid chelates are those where the reacting ligands are glycine, lysine, and leucine. Most preferred is the ferrous amino acid chelate sold under the trade name FERROCHEL® having the reacting ligand as glycine. FERROCHEL® is commercially available from Albion Laboratories, Salt Lake City, Utah. Use of FERROCHEL® herein is particularly useful wherein the composition has low pH.

In addition to these highly bioavailable ferrous and ferric salts, other sources of bioavailable iron can be included in the compositions of the present invention. Other sources of iron particularly suitable for fortifying compositions herein certain iron-sugar-carboxylate complexes. In these iron-sugar-carboxylate complexes, the carboxylate provides the counterion for the ferrous (preferred) or ferric iron. The overall synthesis of these iron-sugar-carboxylate complexes involves the formation of a calcium-sugar moiety in aqueous media (for example, by reacting calcium hydroxide with a sugar, reacting the iron source (such as ferrous ammonium sulfate) with the calcium-sugar moiety in aqueous media to provide an iron-sugar moiety, and neutralizing the reaction system with a carboxylic acid (the "carboxylate counterion") to provide the desired iron-sugar-carboxylate complex). Sugars that can be used to prepare the calcium-sugar moiety include any of the ingestible saccharidic materials, and mixtures thereof, such as glucose, sucrose and fructose, mannose, galactose, lactose, maltose, and the like, with sucrose and fructose being the more preferred. The carboxylic acid providing the "carboxylate counterion" can be any ingestible carboxylic acid such as citric acid, malic acid, tartaric acid, lactic acid, succinic acid, and propionic acid, as well as mixtures of these acids.

These iron-sugar-carboxylate complexes can be prepared in the manner described in (for example) U.S. Pat. Nos. 4,786,510 and 4,786,518, issued Nov. 22, 1988. These materials are referred to as "complexes", but they may, in fact, exist in solution as complicated, highly hydrated, protected colloids; the term "complex" is used for the purpose of simplicity.

Additionally, encapsulated iron is also preferred for use herein. For example, ferrous sulfate encapsulated in a hydrogenated soybean oil matrix may be used, for example, CAP-SHURE® which is commercially available from Bachem Corp., Slate Hill, N.Y. Other solid fats can be used to encapsulate the iron, such as, tristearin, hydrogenated corn oil, cottonseed oil, sunflower oil, tallow, and lard. A particularly preferred encapsulated iron source is microencapsulated SUNACTIVE® Iron, commercially available from Taiyo International, Inc., Edina, Minn., U.S.A. SUNACTIVE® Iron is particularly preferred for use herein due to its water-dispersibility and bioavailability. Additionally, the iron (particularly, ferrous fumarate and ferrous succinate) may be encapsulated with bilayer-forming emulsifiers. See U.S. Pat. No. 5,888,563.

Iron fortified compositions of the present invention preferably contain at least about 1 milligram of iron, more preferably at least about 5 milligrams of iron, and most preferably at least about 10 milligrams of iron all per single serving of the composition (typically, about 236 milliliters of total composition). Typically, from about 10 milligrams to about 25 milligrams of iron is recommended per single serving. Alternatively, the present compositions comprise from 0% to about 0.1%, more preferably from about 0.0001% to about 0.08%, even more preferably from about 0.0002% to about 0.05%, and most preferably from about 0.0002% to about 0.03% of the iron-containing component, by weight of the composition.

As used herein, "magnesium" is inclusive of any compound containing magnesium, including a salt, complex, or other form of magnesium, including elemental magnesium. Acceptable forms of magnesium are well-known in the art.

Magnesium chloride, magnesium citrate, magnesium gluceptate, magnesium gluconate, magnesium hydroxide, magnesium lactate, magnesium oxide, magnesium picolate, and magnesium sulfate are non-limiting, exemplary forms of magnesium for use herein. Additionally, amino acid chelated and creatine chelated magnesium are highly preferred. Amino acid and creatine chelates of magnesium are well-known in the art, and are described in, for example, U.S. Pat. No. 5,516,925; U.S. Pat. No. 5,292,729; and U.S. Pat. No. 4,830,716. These chelates contain one or more natural amino acids or dipeptides, tripeptides or quadrapeptides formed by any combination of these amino acids.

Typically, wherein magnesium is utilized herein, at least about 1 milligram of magnesium is included per single serving of the composition (typically, about 236 milliliters of total composition). More preferably, when used, at least about 50 milligrams of magnesium is included per single serving of the composition. Most preferably, when used, at least about 100 milligrams of magnesium is included per single serving of the composition. About 400 milligrams of magnesium, per single serving of the composition, is recommended for adult humans. Alternatively, the present compositions comprise from 0% to about 1%, more preferably from about 0.001% to about 0.8%, even more preferably from about 0.002% to about 0.6%, and most preferably from about 0.002% to about 0.5% the magnesium-containing component, by weight of the composition.

As used herein, "calcium" is inclusive of any compound containing calcium, including a salt, complex, or other form of calcium, including elemental calcium. Acceptable forms of calcium are well-known in the art.

Preferred sources of calcium include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium realate, calcium tantrate, and calcium lactate, and in particular calcium citrate malate. The form of calcium citrate malate is described in, e.g., U.S. Pat. No. 5,670,344; U.S. Pat. No. 5,612,026; U.S. Pat. No. 5,571,441; U.S. Pat. No. 5,474,793; U.S. Pat. No. 5,468,506; U.S. Pat. No. 5,445,837; U.S. Pat. No. 5,424,082; U.S. Pat. No. 5,422,128; U.S. Pat. No. 5,401,524; U.S. Pat. No. 5,389,387; U.S. Pat. No. 5,314,919; U.S. Pat. No. 5,232,709; U.S. Pat. No. 5,225,221; U.S. Pat. No. 5,215,769; U.S. Pat. No. 5,186,965; U.S. Pat. No. 5,151,274; U.S. Pat. No. 5,128,374; U.S. Pat. No. 5,118,513; U.S. Pat. No. 5,108,761; U.S. Pat. No. 4,994,283; U.S. Pat. No. 4,786,510; and U.S. Pat. No. 4,737,375.

Typically, wherein calcium is utilized herein, at least about 100 milligrams of calcium is included, per single serving of the composition (typically, about 236 milliliters of total composition). More preferably, when used, at least about 200 milligrams of calcium is included per single serving of the composition. Most preferably, when used, at least about 400 milligrams of calcium is included per single serving of the composition. About 1,000 milligrams of calcium, per single serving of the composition, is recommended for adult humans. Preferred compositions of the present invention will comprise from 0% to about 5%, more preferably from about 0.01% to about 0.5%, still more preferably from about 0.03% to about 0.2%, even more preferably from about 0.05% to about 0.15%, and most preferably from about 0.1% to about 0.15% of the calcium-containing component, by weight of the composition.

As used herein, "iodine" is inclusive of any compound containing iodine, including a salt, complex, or other form of iodine, including elemental iodine. Acceptable forms of iodine are well-known in the art. Non-limiting examples of iodine forms include potassium iodide, sodium iodide, potassium iodate, and sodium iodate.

Typically, wherein iodine is utilized herein, at least about 10 micrograms of iodine is included, per single serving of the composition (typically, about 236 milliliters of total composition). More preferably, when used, at least about 15 micrograms of iodine is included, per single serving of the composition. Most preferably, when used, at least about 20 micrograms of iodine is included, per single serving of the composition. From about 10 to about 70 micrograms of iodine, per single serving of the composition, is recommended for adult humans. Preferred compositions of the present invention will comprise from 0% to about 0.1%, more preferably from about 0.00001% to about 0.05%, still more preferably from about 0.00001% to about 0.01%, even more preferably 0.00001% to about 0.005%, and most preferably from about 0.00001% to about 0.001% of the iodine-containing component, by weight of the composition.

Emulsions

Dilute juice beverages of the present invention may optionally comprise from about 0.2% to about 5%, preferably from about 0.5% to about 3%, and most preferably from about 0.8% to about 2%, of a beverage emulsion. This beverage emulsion can be either a cloud emulsion or a flavor emulsion.

For cloud emulsions, the clouding agent can comprise one or more fats or oils stabilized as an oil-in-water emulsion using a suitable food grade emulsifier. Any of a variety of fats or oils may be employed as the clouding agent, provided that the fat or oil is suitable for use in foods and/or beverages. Preferred are those fats and oils that have been refined, bleached and deodorized to remove off-flavors. Especially suitable for use as clouding agents are those fats that are organoleptically neutral. These include fats from the following sources: vegetable fats such as soybean, corn, safflower, sunflower, cottonseed, canola, and rapeseed; nut fats such as coconut, palm, and palm kernel; and synthetic fats. See e.g., U.S. Pat. No. 4,705,691 for suitable fat or oil clouding agents.

Any suitable food grade emulsifier can be used that can stabilize the fat or oil clouding agent as an oil-in-water emulsion. Suitable emulsifiers include gum acacia, modified food starches (e.g., alkenylsuccinate modified food starches), anionic polymers derived from cellulose (e.g., carboxymethylcellulose), gum ghatti, modified gum ghatti, xanthan gum, tragacanth gum, guar gum, locust bean gum, pectin, and mixtures thereof. See e.g., U.S. Pat. No. 4,705,691. Modified starches treated to contain hydrophobic as well as hydrophilic groups, such as those described in U.S. Pat. No. 2,661,349, are preferred emulsifiers for use as herein. Octenyl succinate (OCS) modified starches such as those described in U.S. Pat. No. 3,455,838 and U.S. Pat. No. 4,460,617 are also preferred emulsifiers.

The clouding agent can be combined with a weighting agent to provide a beverage opacifier that imparts a total or partial opaque effect to the beverage without separating out and rising to the top. The beverage opacifier provides the appearance to the consumer of a juice-containing beverage. Any suitable weighting oil can be employed in the beverage opacifier. Typical weighting oils include brominated vegetable oil, glycerol ester of wood rosin (ester gum), sucrose acetate isobutyrate (SAIB) and other sucrose esters, gum damar, colophony, gum elemi, or others known to those skilled in the art. Other suitable weighting agents include brominated liquid polyol polyesters which are nondigestible. See e.g., U.S. Pat. No. 4,705,690.

The cloud/opacifier emulsion may be prepared by mixing the clouding agent with the weighting agent (for opacifier emulsions), the emulsifier and water. The emulsion typically contains from about 0.1% to about 25% clouding agent, from about 1% to about 20% weighting oil agent (in the case of opacifier emulsions), from about 1% to about 30% emulsifiers, and from about 25% to about 97.9% water (or quantum satis).

Flavor emulsions useful in beverage products of the present invention comprise one or more suitable flavor oils, extracts, oleoresins, essential oils and the like, known in the art for use as flavorants in beverages. This component can also comprise flavor concentrates such as those derived from concentration of natural products such as fruits. Terpeneless citrus oils and essences can also be used herein. Examples of suitable flavors include, for example, fruit flavors such as orange, lemon, lime and the like, cola flavors, tea flavors, coffee flavors, chocolate flavors, dairy flavors. These flavors can be derived from natural sources such as essential oils and extracts, or can be synthetically prepared. The flavor emulsion typically comprises a blend of various flavors and can be employed in the form of an emulsion, alcoholic extract, or spray dried. The flavor emulsion can also include clouding agents, with or without weighting agents, as previously described. See e.g., U.S. Pat. No. 4,705,691.

Flavor emulsions are typically prepared in the same manner as cloud/opacifier emulsions by mixing one or more flavoring oils (from about 0.001% to about 20%) with an emulsifying agent (from about 1% to about 30%) and water. (The oil clouding agents can also be present). Emulsions of particles with diameters of from about 0.1 to about 3.0 microns are suitable. Preferably, the particles are about 2.0 microns or less in diameter. Most preferably, the particles are about 1.0 microns or less in diameter. The emulsifying agent coats the particularized flavor oil to aid in preventing coalescence and in maintaining an appropriate dispersion. The viscosity and specific gravity of the flavor emulsion are regulated to be compatible with the finished beverage. See e.g., U.S. Pat. No. 4,705,691.

Flavoring Agents

One or more flavoring agents are recommended for the embodiments of the present invention in order to enhance their palatability. Any natural or synthetic flavor agent can be used in the present invention. For example, one or more botanical and/or fruit flavors may be utilized herein. As used herein, such flavors may be synthetic or natural flavors.

Particularly preferred fruit flavors are exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, grapefruit flavors, and the like. These fruit flavors can be derived from natural sources such as fruit juices and flavor oils, or may alternatively be synthetically prepared.

Preferred botanical flavors include, for example, tea (preferably black and green tea, most preferably green tea), aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardimom, nutmeg, cassia bark, buchu, cinnamon, jasmine, haw, chrysanthemum, water chestnut, sugar cane, lychee, bamboo shoots, vanilla, coffee, and the like. Preferred among these is tea, guarana, ginseng, ginko, and coffee. In particular, the combination of tea flavors, preferably green tea or black tea flavors (preferably green tea), optionally together with fruit flavors has an appealing taste. In another preferred embodiment, coffee is included within the present compositions. A combination of green tea and coffee in the present compositions is often preferred.

The flavor agent can also comprise a blend of various flavors. If desired, the flavor in the flavoring agent may be formed into emulsion droplets which are then dispersed in the beverage composition or concentrate. Because these droplets usually have a specific gravity less than that of water and would therefore form a separate phase, weighting agents (which can also act as clouding agents) can be used to keep the emulsion droplets dispersed in the beverage composition or concentrate. Examples of such weighting agents are brominated vegetable oils (BVO) and resin esters, in particular the ester gums. See *L. F. Green,* Developments in Soft Drinks Technology, Vol. 1, Applied Science Publishers Ltd., pp. 87–93 (1978) for a further description of the use of weighting and clouding agents in liquid beverages. Typically the flavoring agents are conventionally available as concentrates or extracts or in the form of synthetically produced flavoring esters, alcohols, aldehydes, terpenes, sesquiterpenes, and the like.

Coloring Agent

Small amounts of one or more coloring agents may be utilized in the compositions of the present invention. FD&C dyes (e.g., yellow #5, blue #2, red # 40) and/or FD&C lakes are preferably used. By adding the lakes to the other powdered ingredients, all the particles, in particular the colored iron compound, are completely and uniformly colored and a uniformly colored beverage mix is attained. Preferred lakes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and beta-carotene may also be used. Additionally, other natural coloring agents may be utilized including, for example, fruit, vegetable, and/or plant extracts such as grape, black currant, aronia, carrot, beetroot, red cabbage, and hibiscus.

The amount of coloring agent used will vary, depending on the agents used and the intensity desired in the finished product. Generally, if utilized, the coloring agent should be present at a level of from about 0.0001% to about 0.5%, preferably from about 0.001% to about 0.1%, and most preferably from about 0.004% to about 0.1%, by weight of the composition.

Preservatives

Preservatives may or may not be needed for use in the present compositions. Techniques such as aseptic and/or clean-fill processing may be utilized to avoid preservatives.

One or more preservatives may, however, optionally be added to the present compositions. Preferred preservatives include, for example, sorbate, benzoate, and polyphosphate preservatives (for example, sodium hexametapolyphosphate).

Preferably, wherein a preservative is utilized herein, one or more sorbate or benzoate preservatives (or mixtures thereof) are utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof. Sorbate preservatives are particularly preferred. Potassium sorbate is particularly preferred for use in the present invention.

Wherein a composition comprises a preservative, the preservative is preferably included at levels from about 0.0005% to about 0.5%, more preferably from about 0.001% to about 0.4% of the preservative, still more preferably from about 0.001% to about 0.1%, even more preferably from about 0.001% to about 0.05%, and most preferably from about 0.003% to about 0.03% of the preservative, by weight of the composition. Wherein the composition comprises a mixture of one or more preservatives, the total concentration of such preservatives is preferably maintained within these ranges.

Carbonation Component

Carbon dioxide can be introduced into the water which is mixed with a beverage concentrate or into a beverage composition after dilution to achieve carbonation. The carbonated beverage can be placed into a container, such as a bottle or can, and then sealed. Any conventional carbonation methodology may be utilized to make carbonated beverage compositions of this invention. The amount of carbon dioxide introduced into the beverage will depend upon the particular flavor system utilized and the amount of carbonation desired.

Methods of Preparing the Present Compositions

As has been further discovered herein, boron is optimally formulated in accordance with the defined steps described below. Alternatively, the present compositions may be formulated in a variety of manners, including those which will be well-known to those of ordinary skill.

In particular, the present inventor has discovered the following methods, which surprisingly optimize the solubility and bioavailablity of the boron compound used herein. The methods relate to preparing a beverage composition comprising a boron compound, the method comprising the steps of:

a) providing an aqueous solution comprising the boron compound, wherein the pH of the aqueous solution is at least about 2 pH units less than the pKa of the boron compound and wherein the aqueous solution is substantially free of pectin and carbohydrate; and b) combining the aqueous solution with one or more additional beverage components.

With respect to these steps, the boron compound is present within the properly pH adjusted matrix prior to addition of any substantial pectin or carbohydrate. By "substantially free of pectin," it is meant that the aqueous solution comprises less than about 0.5% of pectin, preferably less than about 0.1% of pectin, even more preferably less than about 0.05% of pectin, and most preferably less than about 0.001% of pectin, all by weight of the aqueous solution. By "substantially free of carbohydrate," it is meant that the aqueous solution comprises less than about 0.5% of total carbohydrate, preferably less than about 0.1% of total carbohydrate, even more preferably less than about 0.05% of total carbohydrate, and most preferably less than about 0.001% of total carbohydrate, all by weight of the aqueous solution. The term "carbohydrate" is well-known in the art and includes those compounds having one or more cis-hydroxyl moieties, such as those which are monosaccharides, disaccharides, oligosaccharides, and even longer chain saccharides.

It has been surprisingly discovered that this pH adjustment prevents or discourages complexation of the boron compound which, in turn, leads to enhanced solubility and bioavailability of the compound. The pH of the aqueous solution is consistent with the preferred pH levels provided above, again depending upon the boron compound utilized.

Once the boron compound is present in the aqueous solution, further beverage components, and even those which would ordinarily be susceptible to complexation with boron, may be added. For example, one or more carbohydrates or pectin (including fruit or vegetable juice) may then be combined. Again, components which are ordinarily susceptible to complexation with boron are those having one or more cis-hydroxyl moieties, such as the carbohydrates (e.g., monosaccharides, disaccharides, oligosaccharides, and even longer chain saccharides) and pectin. Those components which would not ordinarily be susceptible to complexation with boron (i.e., components not having a cis-hydroxyl moiety) may be combined at any stage in the process.

Kits of the Present Invention

The compositions of the present invention may be utilized in kits as described herein. The kits of the present invention comprise one or more compositions of the present invention together with information which informs a user of the kit, by words, pictures, and/or the like, that use of the kit will provide one or more general health and 1 or general physiological benefits including, but not limited to, joint health benefits (including relief from, prevention of, and/or inhibition of, arthritis and/or osteoarthritis, as well as enhanced flexibility), bone health benefits (including maintaining and/or building bones), anti-inflammation, and analgesic activity (e.g., pain relief), as well as anti-cancer benefits (including treatment of prostate cancer) and neurological benefits.

In a particularly preferred embodiment, the information is printed on a containment device directly or indirectly containing the composition, e.g., a bottle. As an example, these preferred kits may be in the form of one bottle containing the composition, or may be obtained as a plurality of bottles each containing the composition. For example, the kits may be obtained as one bottle, or cases of four, six, seven (e.g., a weekly supply), or eight bottles co-packaged together. Additionally, monthly kits may be obtained as cases of, for example, twenty-eight or thirty bottles co-packaged together. In this instance, as a non-limiting example, the information may be printed on each individual bottle and/or on a containment device (e.g., a box) containing the bottles.

As used herein, the information may be conveyed through words, pictures, symbols, and/or other visible descriptors. Such information need not utilize the actual words used herein, for example, "joint", "bone", "human", "mammal", "arthritis", or "boron" but rather use of words, pictures, symbols, and the like conveying the same or similar meaning are contemplated within the scope of this invention. What is important is that the consumer, who may not necessarily be skilled in the art, understand the utility of the claimed invention.

Methods of Using the Present Invention

The methods of the present invention comprise orally administering (i.e., through ingestion) a composition of the present invention to a mammal, preferably a human, to treat joint dysfunction, bone dysfunction, pain, and/or inflammation. The compositions are preferably ingested by mammals which experience joint and/or bone dysfunction or those who desire to maintain current joint and/or bone function (i.e., prophylactic use). The compositions of this invention may also be ingested as a supplement to normal dietetic requirements. Frequency of administration is not limited, however, such administration is typically at least once weekly, more preferably at least 3 times weekly, and most preferably at least once daily. Administration will typically be ongoing.

As used herein, the term "orally administering" with respect to the mammal (preferably, human) means that the mammal ingests or is directed to ingest one or more compositions of the present invention for one or more of the purposes described herein, including treating joint dysfunction, bone dysfunction, analgesic activity, and/or inflammation, as well as cancer (including treatment of prostate cancer) and neurological conditions. For example, such direction may be oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" means through words, pictures, symbols, and/or other visible descriptors. Such direction need not utilize the actual words used herein, for example, "joint", "bone", "human", "mammal", "arthritis", or "boron" but rather use of words, pictures, symbols, and the like conveying the same or similar meaning are contemplated within the scope of this invention.

EXAMPLES

The following are non-limiting examples of compositions used in accordance with the present invention. Moreover, non-limiting analytical methods are described. The following examples are provided to illustrate the invention and are not intended to limit the scope thereof in any manner.

Example 1

The pKa of the boron compound utilized herein may be determined as follows. The pKa values may be determined by preparing a saturated aqueous solution of the boron compound and acidifying the solution with hydrochloric acid to below the expected pKa value. Using an auto titrator, titrate the solution according to standard methods. The pKa of the boron compound is the pH at which the inflection point occurs in the resulting titration curve.

Example 2

The following beverage composition is prepared having the following components in the indicated amounts:

| Component | Amount (in weight percent, except as indicated) |
| --- | --- |
| Water | Quantum Satis |
| Boron Compound | 3 mg/236 mL of beverage composition |
| Glucosamine Hydrochloride | 0.75 |
| Crystalline Fructose | 8.8 |
| Malic Acid | 0.22 |
| Citric Acid | 0.64 |
| Calcium Hydroxide | 0.24 |
| Pre-mix | 1.35 |
| Ascorbic Acid | 0.07 |

The Pre-mix for this beverage composition is prepared having the following components in the indicated amounts:

| Component | Amount (in weight percent) |
| --- | --- |
| Water | Quantum Satis |
| Sodium Benzoate | 0.07 |
| Citric Acid | 1.5 |
| Juice Concentrates | 63.9 |
| Flavors | 8.9 |
| Color | 0.6 |

To prevent or minimize undesirable boron complexes from forming during the processing and formulation of beverages containing boron compounds, all ingredients are at the appropriate pH conditions prior to the addition of the boron compound (i.e., at least about 2 pH units less than the pKa of the boron compound). The addition of ingredients or pre-mixes, after addition of the boron compound should also be at these appropriate pH conditions.

In this example, citric acid and malic acid are added to water and dissolved. The calcium hydroxide is added. The fructose, glucosamine hydrochloride, and ascorbic acid are then added. The boron compound (for example, boric acid or boron citrate) is then added to deliver 3 mg of boron per single serving and dissolved. The acidified pre-mix is added.

Example 3

The following carbonated orange beverage composition is prepared by combining all desired ingredients except for the carbonated water (tending to have a basic character). The pH of the composition is adjusted to 4 using citric acid, as needed. The boron compound is added to deliver about 3 mg of boron per 236 mL of final beverage composition. The carbonated water is finally added to provide the final beverage composition.

Example 4

The following fruit and vegetable juice composition is prepared having the following components in the indicated amounts:

| Component | Amount (in weight percent, excepted as indicated) |
| --- | --- |
| Water | Quantum Satis |
| Boron Compound | 3 mg/236 mL of beverage composition |
| Carrot Juice | 10 |
| Passion Fruit Juice | 5 |
| White Grape Juice | 5 |
| Citric Acid | 0.86 |

Combine the water, carrot juice, passion fruit juice, white grape juice, and citric acid. Mix these ingredients until a solution is formed. The boron compound (e.g., boron citrate) is added to deliver about 2 mg of boron per 236 mL of the composition. Dissolve and mix until uniform; contain composition in separate 236 mL capacity bottles.

Example 5

The following juice composition is prepared having the following components in the indicated amounts:

| Component | Amount (in weight percent, except as indicated) |
| --- | --- |
| Water (pH adjusted to 4.5 using citric acid) | Quantum Satis |
| Boric Acid | 3 mg/236 mL of juice composition |
| Orange Juice Concentrate | 50 |

Dissolve the boric acid in the pH adjusted water. Add this solution to the juice concentrate and mix until uniform.

What is claimed is:

1. A beverage composition comprising:
   a) a boron compound; and
   b) at least about 10% water, by weight of the composition;
   wherein the pH of the composition is at least about 3 pH units less than the pKa of the boron compound, and wherein the composition is substantially free of complexed boron.

2. The composition according to claim 1 wherein the pH of the composition is about 7.2 or less.

3. The composition according to claim 2 wherein the pKa of the boron compound is about 4 or greater.

4. The composition according to claim 3 which is a ready-to-drink beverage composition comprising at least about 50% water, by weight of the composition.

5. The composition according to claim 4 wherein the pH of the composition is about 5 or less and the pKa of the boron compound is about 9 or greater.

6. The composition according to claim 2 further comprising pectin.

7. The composition according to claim 6 comprising fruit juice.

8. The composition according to claim 7 further comprising one or more nutrients additional to the boron.

9. The composition according to claim 8 which is a ready-to-drink beverage composition comprising at least about 50% water, by weight of the composition.

10. The composition according to claim 9 wherein the boron compound is selected from the group consisting of boric acid, boron citrate, and mixtures thereof.

11. The composition according to claim 10 wherein the pH of the composition is from about 2.5 to about 4.

12. The composition according to claim 11 wherein at least one of the nutrients is selected from the group consisting of calcium and vitamin D.

13. The composition according to claim 12 wherein at least one of the nutrients is calcium.

14. The composition according to claim 2 further comprising one or more further chondroprotective agents.

15. The composition according to claim 14 wherein at least one of the chondroprotective agents is an amino sugar or a salt thereof.

16. The composition according to claim 15 wherein at least one of the chondroprotective agents is a glucosamine salt.

17. The composition according to claim 16 further comprising fruit juice.

18. A method of preparing a beverage composition comprising a boron compound, the method comprising the steps of:

a) providing an aqueous solution comprising the boron compound, wherein the pH of the aqueous solution is at least about 3 pH units less than the pKa of the boron compound and wherein the aqueous solution is substantially free of pectin and carbohydrate; and b) combining the aqueous solution with one or more additional beverage components.

19. A method according to claim 18 wherein at least one of the additional beverage components is selected from the group consisting of fruit juice and carbohydrates.

20. A method of treating a condition selected from the group consisting of joint dysfunction, bone dysfunction, pain, inflammation, and combinations thereof, comprising orally administering to a mammal a composition according to claim 1.

21. A method according to claim 20 wherein the administration is once daily.

22. A kit comprising:

(a) a composition according to claim 1; and (b) information that use of the composition is useful for one or more health benefits wherein at least one of the benefits is selected from the group consisting of joint health benefits, bone health benefits, analgesic activity, and anti-inflammation.

* * * * *